US006541487B1

(12) United States Patent
Cutler

(10) Patent No.: US 6,541,487 B1
(45) Date of Patent: Apr. 1, 2003

(54) PDE III INHIBITORS FOR TREATING SEXUAL DYSFUNCTION

(75) Inventor: Neal R. Cutler, Los Angelos, CA (US)

(73) Assignee: R.T. Alamo Ventures I, LLC, Beverly Hills, CA (US)

( * ) Notice: Subject to any disclaimer, the term of this patent is extended or adjusted under 35 U.S.C. 154(b) by 0 days.

(21) Appl. No.: 09/653,959

(22) Filed: Sep. 1, 2000

Related U.S. Application Data

(63) Continuation-in-part of application No. 09/262,715, filed on Mar. 4, 1999, now Pat. No. 6,187,790, and a continuation-in-part of application No. 09/260,099, filed on Mar. 2, 1999, now Pat. No. 6,132,757, which is a continuation-in-part of application No. 09/175,395, filed on Oct. 19, 1998, now Pat. No. 6,132,753, which is a continuation-in-part of application No. 09/071,457, filed on May 1, 1998, now Pat. No. 6,110,489.

(51) Int. Cl.[7] ............................................. A61K 31/47
(52) U.S. Cl. ....................................... 514/312; 514/311
(58) Field of Search ................................... 514/312, 311

(56) References Cited

U.S. PATENT DOCUMENTS 6,037,346 A    3/2000  Doherty, Jr. et al. ........ 514/258
6,110,489 A  * 8/2000  Cutler ........................ 424/449
6,127,363 A   10/2000  Doherty, Jr. et al. ........ 514/220
6,132,753 A  * 10/2000 Cutler ........................ 424/423
6,132,757 A  * 10/2000 Cutler ........................ 424/434
6,143,762 A  * 11/2000 Nash et al. .................. 514/307
6,156,753 A   12/2000  Doherty, Jr. et al. ........ 514/252
6,187,790 B1 *  2/2001 Cutler ........................ 514/312
6,194,433 B1 *  2/2001 Cutler ........................ 514/312
6,258,373 B1 *  7/2001 Cutler ........................ 424/434
6,303,135 B1 * 10/2001 Cutler ........................ 424/423
6,469,012 B1   10/2002 Ellis et al.

FOREIGN PATENT DOCUMENTS

WO     WO 99/56666       11/1999

* cited by examiner

Primary Examiner—Theodore J. Criares
Assistant Examiner—Jennifer Kim
(74) Attorney, Agent, or Firm—McDermott, Will & Emery

(57) ABSTRACT

Compositions that are selective PDE III inhibitors and that are effective to treat sexual dysfunction in males and females, including, but not limited to, erectile dysfunction in males. The compositions comprise halogenated quinolines, isoquinolines, quinolones, thioquinolones and 2-oxoquinolones, including derivatives thereof. The compounds can be taken orally or by a number of different routes or can be used to coat the interior of a condom to induce erection.

13 Claims, No Drawings

PDE III INHIBITORS FOR TREATING SEXUAL DYSFUNCTION

RELATED APPLICATIONS

This application is a continuation-in-part of application Ser. No. 09/262,715, filed Mar. 4, 1999, now U.S. Pat. No. 6,187,790, and a continuation-in-part of application Ser. No. 09/260,099 filed Mar. 2, 1999, now U.S. Pat. No. 6,132,757, which is a continuation-in-part of application Ser. No. 09/175,395 filed Oct. 19, 1998, now U.S. Pat. No. 6,132,753, which is a continuation-in-part of application Ser. No. 09/071,457 filed May 1, 1998, now U.S. Pat. No. 6,110,489.

FIELD OF THE INVENTION

The present invention relates to methods for the treatment of sexual dysfunction in males and females, including but not limited to erectile dysfunction in males.

BACKGROUND

Impotence or erectile insufficiency is a widespread disorder that is thought to affect about twelve percent of adult men under age forty-five, about twenty percent of men at age sixty, and about fifty-five percent of men at age seventy-five. Similar to male sexual dysfunction, the prevalence of female sexual dysfunction has been shown to increase with age and be associated with the presence of vascular risk factors and the development of menopause.

There is more than one cause of erectile dysfunction. For example, erectile dysfunction can be psychological, resulting from anxiety or depression, with no apparent somatic or organic impairment. Such erectile dysfunction, which is referred to as "psychogenic", is responsible for about fifteen to twenty percent of cases of impotence. In other cases, the erectile dysfunction is associated with atherosclerosis of the arteries supplying blood to the penis; such dysfunction is referred to as "arteriogenic" or "atherosclerotic." About forty to sixty percent of cases of impotence are arteriogenic in origin.

In still other cases, there is leakage from veins in the penis such that sufficient pressure for an erection can be neither obtained nor maintained. This dysfunction is referred to as "venous leakage," or "abnormal drainage". This condition is often exacerbated by the presence of some arteriogenic dysfunction whereby the supply of blood to the penis is impaired. In still other cases, the dysfunction is associated with a neuropathy, such as nerve damage arising from, for example, surgery or a pelvic injury, in the nervous system affecting the penis. Such a dysfunction is referred to as "neurogenic" and this accounts for about ten to fifteen percent of cases of impotence.

There is also a high incidence of erectile insufficiency among diabetics, particularly those with insulin-dependent diabetes mellitus. Erectile dysfunction in diabetics is often classified as "diabetogenic," although the underlying dysfunction is usually neurogenic associated with neuropathy, but may be arteriogenic or neurogenic and arteriogenic. About half of diabetic males suffer from erectile insufficiency, and about half of the cases of neurogenic impotence are in diabetics.

Additionally, erectile insufficiency is sometimes a side effect of certain drugs, such as beta-blockers that are administered to reduce blood pressure in persons suffering from hypertension, or drugs administered to treat depression or anxiety. Excessive alcohol consumption has also been linked to erectile insufficiency. These forms of erectile insufficiency may be regarded as a subset of neurogenic or psychogenic insufficiency.

Diagnosis of Male Erectile Dysfunction

Determination whether a human male is suffering from impotence that is substantially only neurogenic or psychogenic is readily made by a person skilled in the art using a number of readily available diagnostic procedures. Thus, a male suffering from impotence can first be given a physical examination with particular attention to possible penile and scrotal pathology, whereby any anatomical deficiency precluding an erection sufficient for vaginal penetration can be detected. In the absence of such an anatomical deficiency, the male can be subjected to tests, whereby penile venous leakage or severe or untreatable atherosclerosis can be detected.

Such tests include determination of the penobrachial blood pressure index (PBPI), doppler investigation of the penile arteries, and a papaverine test. The PBPI is the penile systolic blood pressure divided by the systolic blood pressure determined at one of the arms. These blood pressures can be determined by any number of standard techniques. Thus, the penile systolic blood pressure can be determined by (i) placing an inflatable cuff around the base of the free part of the penis in the flaccid state which is capable of being used to apply variable pressure, readable from a gauge, to an object around which the cuff is placed, (ii) localizing the penile arteries with a Doppler ultrasound probe (e.g., 8 MHz probe, such as the Mini Doplex D500 available from Huntleigh Technology, Luton, United Kingdom), and then (iii) inflating and deflating the cuff and ascertaining the pressure at which the Doppler sound reappears.

The pressure at which the Doppler sound reappears is the penile systolic blood pressure. A male's penile blood pressure is regarded as normal if his PBPI is >0.80. With regard to Doppler investigation, each of the two penile cavernous arteries is investigated distal to the aforementioned cuff using the Doppler ultrasound problem. The function of each of the two arteries is assessed by Doppler ultrasound using an arbitrary scale of 0, 1, 2 or 3, where 0 means that the function is so deficient that the artery cannot be located and 3 means that the artery is well enough that maximal Doppler sound is observed.

In the papaverine test, a tourniquet is placed at the base of the free part of the penis and tightened and then, with the patient seated, 30 mg of papaverine in 1 ml of a physiological acceptable fluid (e.g., physiological saline or phosphate-buffered saline) is injected into the penile cavernous body. In persons suspected of having impotence due to a suprasacral nerve lesion or a psychogenic dysfunction, only 15 mg of papaverine is administered, because of the high incidence of papaverine-induced priapism in such cases.

Five minutes after the injection, the tourniquet is removed and an ultrasound Doppler investigation of the penile cavernous arteries is carried out as described above. The function of the arteries is regarded as normal if both of them score a 3 on the arbitrary scale. After the Doppler investigation, penile vibration, at about a 4 Hz with an amplitude of about 1.2 mm (carried out with, e.g., a Vibrector from Multicept, Gentofte, Denmark) is carried out for five to ten minutes and then erectile response is evaluated.

Erectile response is classified as full rigidity, if the angle between the penis and the legs in the standing position is >90°, and tumescence or no response if the angle is less than or equal to 45°. An impotent male, who does not have an anatomical deficiency that would preclude having an erection sufficient for vaginal penetration, who has a PBPI>0.80, who has scores of 2 or 3 in Doppler ultrasound investigations of both of the cavernous arteries of the penis, after papaverine injection and vibration as described above, is suffering from impotence that is "substantially only neurogenic or psychogenic" in origin.

It is possible that atherosclerosis or venous leakage contributes to such impotence, and atherosclerosis likely does contribute if the score is less than 3 in the Doppler investigation of one or both of the cavernous arteries after papaverine injection; but any venous leakage or atherosclerosis in such impotence is not untreatable and, consequently, is not a substantial factor in the impotence and such atherosclerosis, if any, is less than severe.

Impotence, which is a side-effect of drugs such as beta-blockers, is deemed to be neurogenic impotence in the present specification. Similarly, impotence which is a result of alcoholism or excessive consumption of alcohol, is deemed to be neurogenic or psychogenic impotence, for purposes of the present specification. Thus, a male who is diagnosed in accordance with the present specification as suffering from impotence that is "substantially only neurogenic or psychogenic" in origin is suffering from impotence that is substantially only neurogenic, psychogenic or neurogenic and psychogenic in origin, even though an underlying cause of the impotence has been identified as a side-effect of a drug, alcoholism or excessive consumption of alcohol.

Generally, a male with a PBPI less than about 0.60, with scores of 0 in Doppler investigations of both penile cavernous arteries (after papaverine injection as described above), and with a less than fully rigid erection after papaverine injection and vibration will have impotence caused by "untreatable" atherosclerosis. Methods are available to ascertain whether impotence is untreatable because of venous leakage.

One method of ascertaining whether untreatable venous leakage is a cause of impotence is by cavernosometry, optionally supplemented with cavernosography. See, e.g., Delcour et al., *Radiology* 161: 799 (1986); Porst et al., *J. Urol.* 137: 1163 (1987); Lue et al., *J. Urol.* 37: 829 (1987). Cavernosometry can be done using, both before and after intracavernosal injection of 60 mg of papaverine (in 1 ml of physiological saline), infusion of physiological saline through a 19-gauge needle into one corpus cavernosum with a 21-gauge needle inserted into the other corpus cavernosum for measurement of intracorporal pressure (which is recorded on a plotter).

The infusion rates needed to induce and maintain an erection are measured. If the infusion rate needed to maintain an erection is greater than 50 ml/min before administration of the papaverine and greater than 15 ml/min after administration of the papaverine, untreatable venous leakage is present. As long as an erection can be achieved at some flow rate less than about 100 ml/min before injection of the papaverine and less than about 50 ml/min after the injection of papaverine, it might be possible, using cavernosography, to locate the venous lesion associated with the leakage, and thereby confirm the diagnosis based on cavernosometry and provide information for possible surgical correction for the leakage. In the cavernosography, the penis is X-rayed, both before and after intracavernosal injection of 60 mg papaverine (in 1 ml of physiological saline), while infusing contrast medium into the corpus cavernosum (e.g., through a 19-gauge needle) at a flow rate that maintains an erection during the x-raying. Numerous contrast media suitable for the procedure are available in the art; these are typically aqueous solutions of iodinated compounds that provide between about 180 mg/ml and about 360 mg/ml of iodine. Examples are a solution of iohexol providing 240 mg/ml of iodine sold by Winthrop Pharmaceuticals, New York, N.Y., USA, and a solution of iopamidol providing 300 mg/ml iodine sold by Astra Meditec, Goteborg, Sweden. Typically 50–100 ml of the contrast medium will be employed for each x-ray (i.e., before and then after the injection of papaverine). In the cavernosometry and cavernosography, 30 mg papaverine (in 1 ml physiological saline) coupled with stimulation by vibration can be employed in place of 60 mg papaverine (in 1 ml physiological saline).

Treatment of Male Erectile Dysfunction

A number of methods to treat impotence are available. These treatments include pharmacological treatments, surgery and, in cases of psychogenic dysfunction, psychological counseling is sometimes effective. Psychogenic impotence often can be cured by counseling coupled with a demonstration to the patient that he is capable of having a full erection by inducing such an erection once or a few times in the patients. Insufficiency due to excessive alcohol consumption is sometimes cured by reducing or elimination such consumption.

In the rare cases, where the insufficiency is physical because of venous leakage, surgery can usually be employed to repair the venous lesion and thereby either cure the insufficiency or, if there remains an erectile insufficiency after repair of the venous lesion, render the insufficiency amenable to treatment by pharmacological methods. Also, penile implants, which provide a mechanical means to produce an erection sufficient for vaginal penetration, are widely used to treat impotence. In recent years, implants have been employed, especially in cases where pharmacological intervention is ineffective, which are usually cases of severe atherogenic impotence. Treatment of impotence with penile implants, however, entails serious disadvantages. Such treatment requires surgery and necessitates total destruction of the erectile tissues of the penis, forever precluding normal erection.

Pharmacological methods of treatment are also available. Such methods, however, have not proven to be highly satisfactory and can be accompanied by severe side-effects. Papaverine is now widely used to treat impotence, although papaverine is ineffective in overcoming impotence due, at least in part, to severe atherosclerosis. Papaverine is effective in cases where the dysfunction is psychogenic or neurogenic and severe atherosclerosis is not involved. Injection of papaverine, a smooth muscle relaxant, or phenoxybenzamine, a non-specific blocker and hypotensive, into a corpus cavernosum has been found to cause an erection sufficient for vaginal penetration. Also, in cases where severe atherosclerosis is not a cause of the dysfunction, intracavernosal injection of phentolamine, an α-adrenergic blocker, causes an erection sufficient for vaginal penetration. The resulting erection is one of significantly shorter duration than that induced by intracavernosal injection of papaverine or phenoxybenzamine and is of such short duration that satisfactory sexual relations are difficult or impossible.

Treatment of impotence with papaverine or phenoxybenzamine often results in priapism, a locking-up of an erection for a long period of time, typically a few hours and sometimes longer than twenty-four hours. Priapism is a serious, deleterious side effect of treatment of erectile insufficiency with these drugs. Beyond the embarrassment that may be caused for some men, priapism is usually painful, irreversibly damages erectile tissue, and, to be relieved, requires bleeding or pharmacological intervention, such as injection of a sympathomimetic drug, such as adrenaline.

Even if priapism does not occur with use of papaverine, such use is associated with a painful, burning sensation in the first two or so minutes after the injection and there are indications that repeated use of papaverine causes undesirable, extensive intracavernous fibrosis. Further, as indicated above, impotence arising from severe atherosclerosis is not susceptible to treatment with papaverine, phenoxybenzamine, phentolamine or papaverine together with phentolamine. In any case, phenoxybenzamine is not suitable for use in treating impotence because it is a carcinogen.

Thus, although impotence is a ubiquitous problem, there are few satisfactory methods available for treating this disorder. Because of the relatively invasive intervention involved and the high failure rate of penile prostheses, surgical approaches provide unattractive alternatives. A safe pharmacological approach to the treatment of impotence is still to be achieved.

In humans, penile erection is dependent upon the relaxation of the smooth muscle tone in cells of the corpus cavernosum. This relaxation is dependent on the presence of adequate levels of a cyclic guanosine monophosphate (cyclic GMP) and cyclic adenosine monophosphate (cyclic AMP), which are regulated by phosphodiesterase (PDE) isoenzymes. Cyclic GMP and cyclic AMP are secondary messengers that can be degraded by PDE isoenzymes. The second messenger signal pathway is essential for cavernous smooth muscle relaxation.

There are seven known types of phosphodiesterase isoenzymes which, if inhibited, affect different functions of the body. For Example, type I phosphodiesterase (PDE I), if inhibited, affects among others the human cardiac ventricle; type IV phosphodiesterase (PDE IV), if inhibited, affects among other organs and tissue, the human skeletal muscle; while type VI phosphodiesterase (PDE VI), if inhibited, affects the human retna. *Joint Clinical Review*, page 4, Jan. 22, 1998. Types III and V phosphodiesterase (PDE III and PDE V, respectively), if inhibited, are known to affect, among other organs and tissue, the human corpus cavernosum. Stief et al, *J. Urol.* 159(4): 1390–3 (1998). For example, the hydrolysis of the second messenger cyclic AMP by PDE III is known to play an important regulatory role in the relaxation of cavernous smooth muscle of the penis. Kuthe et al., *Chem. Biol. Interact.* 119–120: 593–8 (1999). On the other hand, Sildenafil, commonly known as Viagra®, is a selective PDE V inhibitor. Sildenafil selectively increases cyclic GMP levels in coronary vascular smooth muscle tissue, but produces no change in cyclic AMP levels. Sildenafil exhibits negligible inhibition of PDE III. Wallis et al., *Am. J. Cardiol.* 83 (5A): 3C–12C (1999).

Applicant has discovered compounds, that are selective PDE III inhibitors and that are useful in the treatment of sexual dysfunction in both males and females. Moreover, the compounds minimize the undesirable side effects associated with papaverine, phenoxybenzamine, and phentolamine. Papaverine, for example, is a non-selective inhibitor of PDE, i.e., papaverine will inhibit all types of phosphodiesterase, not just PDE III. Accordingly, using a selective inhibitor specific to PDE III which affects the human corpus cavernosum in the treatment of patients with sexual dysfunction would have a beneficial therapeutic effect.

SUMMARY OF THE INVENTION

It is an object of the present invention to provide a method for treating sexual dysfunction in males and females with inhibitor compounds that are selective for inhibiting PDE III.

It is a further object of the invention to provide for a method of treating sexual dysfunction in males and females, in particular, male erectile dysfunction with quinolines, isoquinolines and quinolones, including derivatives thereof, which are PDE III inhibitors.

It is still a further object of the invention to provide a method for using thioquinolone or sulphinyl or suphonyl derivatives, PDE III inhibitors, to treat sexual dysfunction in males and females, in particular, male erectile dysfunction.

It is still a further object of the invention to use flosequinan (7-fluoro-1-methyl-3-methylsulphinyl-4-quinolone), a PDE III inhibitor, to treat sexual dysfunction in males and females, in particular, male erectile dysfunction.

It is still a further object of the invention to use a 2-oxoquinoline and derivatives thereof, PDE III inhibitors, to treat sexual dysfunction in males and females.

It is still a further object of the invention to treat sexual dysfunction in both males and females with cilostazol (6-[4-(1-cyclohexyl-5-tetrazoyl)butoxy]-1,2,3,4-tetrahydro-2-oxoquinoline), also known as 6-[4-(1-cyclohexyl-1H-tetrazol-5-yl)-butoxy]-3,4-dihydro2(1H)-quinoli-none and 6-[4-(1-cyclohexyl-1H-tetrazol-5-yl)butoxy]-3,4-dihydrocarbostyril.

It is still a further object of the invention to treat sexual dysfunction in both males and females with metabolites of cilostazol, in particular, monohydroxycilostazol, monohydroxy- dehydrocilostazol, 3,4-dihydro-6-hydroxy-2(1H)-quinolone, their conjugates and dehydro-cilostazol.

It is still a further object of the invention to coat the interior of a condom with the selective PDE III inhibitors of the invention to induce erection.

Definitions

As used herein, the term "quinoline" refers to chemical compositions comprising quinoline as set forth in the following structure:

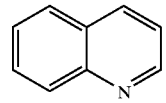

as well as other forms of quinoline such as isoquinoline:

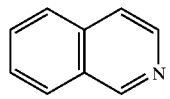

and 2-oxoquinoline:

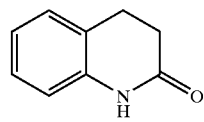

As used herein, the phrase "derivatives of quinoline" refers to chemical compositions comprising quinoline with a chemical group attached, including halogenated quinoline, e.g., 5-bromoquinoline:

and 1-methylisoquinoline:

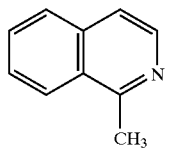

As used herein, the phrase "methylsulphinyl derivatives of quinoline" refers to chemical compositions comprising quinoline with a methylsulphinyl group attached. Examples include flosequinan (7-fluoro-1-methyl-3-methylsulphinyl-4-quinolone):

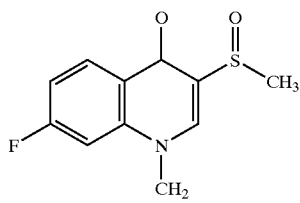

and sulfone metabolites of flosequinan:

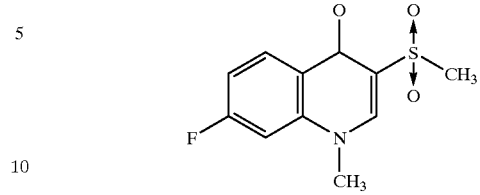

As used herein, "cilostazol" refers to a chemical compound as set forth in the following structure:

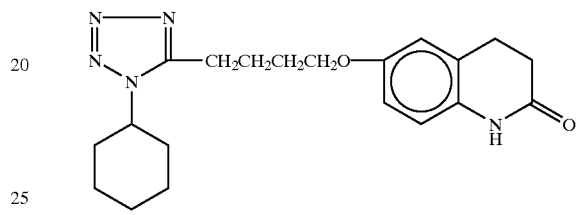

As used herein, a patient who is "free from cardiac disease" and a patient who is "free from symptoms of cardiac disease" indicate that the patient has not been diagnosed with angina, myocardial infarction, congestive heart failure and that symptoms of angina, ischemia, myocardial infarction, congestive heart failure have not been detected, respectively.

As used herein, "drugs that have hypotensive effects" are those drugs which, when administered, cause the patient's end-diastolic blood pressure to be reduced. Nitrates are commonly used drugs which have hypotensive effects.

As used herein, "nitrates" are compounds that contain the —$NO_3$— moiety. Nitrates typically used in the clinic are shown in Table 1.

As used herein, "nitrites" are compounds that contain the —$NO_2$— moiety. Nitrites typically used in the clinic are shown in Table 1.

TABLE 1

Organic Nitrates Available for Clinical Use

| NONPROPRIETARY NAMES AND TRADE NAMES | CHEMICAL STRUCTURE | PREPARATIONS, USUAL DOSES, AND ROUTES OF ADMINISTRATION* | |
|---|---|---|---|
| Amyl nitrite (isoamyl nitrite) | $H_3C$<br>\<br>$CHCH_2CH_2ONO$<br>/<br>$H_3C$ | Inh: | 0.18 or 0.3 ml, inhalation |
| Nitroglycerin (glyceryl trinitrate; NITRO-BID, NITROSTAT, NITROL, NITRO-DUR, others) | $H_2C$—O—$NO_2$<br>\|<br>$HC$—O—$NO_2$<br>\|<br>$H_2C$—O—$NO_2$ | T:<br>S:<br>C:<br>B:<br>O:<br>D:<br>IV: | 0.15 to 0.6 mg as needed<br>0.4 mg per spray as needed<br>2.5 to 9 mg two to four times daily<br>1 mg every 3 to 5 h<br>1.25 to 5 cm (½ to 2 in.), topically to skin every 4 to 8 h<br>1 disc (2.5 to 15 mg) every 24 h<br>5 μg/min; increments of 5 μg/min |

TABLE 1-continued

Organic Nitrates Available for Clinical Use

| NONPROPRIETARY NAMES AND TRADE NAMES | CHEMICAL STRUCTURE | PREPARATIONS, USUAL DOSES, AND ROUTES OF ADMINISTRATION* |
|---|---|---|
| Isosorbide dinitrate (ISORDIL, SORBITRATE, DILATRATE, others) | ![structure] | T: 2.5 to 10 mg every 2 to 3 h<br>T(C): 5 to 10 mg every 2 to 3 h<br>T(O): 10 to 40 mg every 6 h<br>C: 40 to 80 mg every 8 to 12 h |
| Isosorbide-5-mononitrate (IMDUR, ISMO, others) | ![structure] | T: 10 to 40 mg twice daily<br>C: 60 mg daily |
| Erythrityl tetranitrate (CARDILATE) | $H_2C-O-NO_2$<br>$HC-O-NO_2$<br>$HC-O-NO_2$<br>$H_2C-O-NO_2$ | T: 5 to 10 mg as needed<br>T(O): 10 mg three times daily |

*B, buccal (transmucosal) tablet: C, sustained-release capsule or tablet; D, transdermal disc; Inh, inhalant; IV, intravenous injection; O, ointment; S, lingual spray; T, tablet for sublingual use; T(C), chewable tablet; T(O), oral tablet or capsule.

As used herein, "corpus cavernosum" means the columns of erectile tissue forming the body of the clitoris (c. cavernosum clitoridis) or the penis (c. cavernosum penis).

As used herein, the term "erectile dysfunction" refers to certain disorders of the cavernous tissue of the penis and the associated facia which produce impotence, i.e., the inability to attain a sexually functional erection.

As used herein "condom" refers to a sheath or cover to be worn over the penis in coitus to prevent impregnation or infection.

As used herein "standard injection" refers to the placement of a pharmaceutical composition into a subject with a hypodermic needle. For example, such injection can be made subcutaneously, intravenously, intramuscularly and intracavernosally.

As used herein, "intracavernosal" injection is injection into the corpus cavernosum of the penis.

As used herein, an "erection" refers to the condition of a penis whereby it is at least semi-rigid as opposed to being in a flaccid state.

As used herein, "by oral administration" refers to the introduction of a pharmaceutical composition into a subject by way of the oral cavity in aqueous liquid or solid form.

As used herein, "cutaneously" refers to the introduction of a pharmaceutical composition into a subject by application to the surface of the skin such that the composition is absorbed into the subject.

As used herein, "transurethrally" refers to the introduction of a pharmaceutical composition to the urethra of a subject such that the composition is absorbed into the subject.

As used herein, "sufficient for vaginal penetration" refers to the state of an erection such that the penis is capable of entering a vagina without manual manipulation.

As used herein, "sexual stimulation" refers to activity that would induce an erection in a male without erectile dysfunction such as sexually explicit media, manual manipulation, vibration, or live erotic entertainment.

As used herein, "sexually explicit media" refers to films, videos, books, magazines or photographs that depict sexual activity.

As used herein "single dosage" refers to a pharmaceutical composition of a formulation that is capable of achieving its intended effect in a single application.

DETAILED DESCRIPTION OF THE INVENTION

The present invention contemplates the use of compositions that are selective PDE III inhibitors and that are effective to treat sexual dysfunction in males and females, including, but not limited to, erectile dysfunction in males. The compositions comprise halogenated quinolines, isoquinolines, quinolones, thioquinolones and 2-oxoquinolones, including derivatives thereof. The compositions are effective to induce an erection in a human male suffering from impotence of any origin, other than anatomical deficiencies, i.e., lacking a penis or a significant portion thereof, that preclude an erection sufficient for vaginal penetration. In particular, these compositions may be used to induce an erection in a male suffering from impotence caused by severe atherosclerosis, and also impotence that is neurogenic or psychogenic in origin.

The halogenated quinoline contemplated by the present invention is 5-bromoquinoline. The isoquinolines include 5-nitroisoquinoline, 8-nitroisoquinoline and 1-methylisoquinoline. One skilled in the art can readily produce such quinoline and isoquinoline derivatives as set forth in McMurry, *Organic Chemistry. 2nd Ed.*, Brooks/Cole Publishing, Belmont, Calif. (1988), pages 1044–1045 and 1076.

The present invention further contemplates the use of methylthio and methylsulphinyl derivatives of quinoline. In a preferred embodiment, the methylsulphinyl derivative is flosequinan (7-fluoro-1-methyl-3-methylsulphinyl-4-quinolone). Methods of producing methylsulphinyl and methylthio derivatives of quinoline, including flosequinan, are set forth in U.S. Pat. Nos. 5,079,264 and 5,011,931 to MacLean et al.

The action of flosequinan in the body is not precisely understood. Its activity in the body is attributed to flosequinan itself, as well as its sulfone metabolite. It has been reported to be useful to some degree in the treatment of heart failure. See Kelso et al., *J. Cardiovasc. Pharmacol.* 25: 3 76 (1995). However, its action appears to have little effect in patients with end-stage failure and does not affect mortality or arrhythmias following coronary artery ligation. See Perreault et al., *Br. J. Pharmacol.* 106: 511(1992) and Jones et al., *Br. J. Pharmacol.* 108: 1111(1993).

Flosequinan has been reported to be a selective inhibitor of PDE III, but for cardiac activity. See Gristwood et al., *Br. J. Pharmacol.* 105: 985 (1992). But, it has also been reported that the phosphodiesterase inhibition by flosequinan, as relevant to its efficacy in heart failure, is questionable. See Frodsham et al., *Eur. J. Pharmacol.* 211: 383 (1992). It has not been reported that flosequinan, as a selective inhibitor of PDE III activity, is useful for treating sexual dysfunctions. Thus, the application of flosequinan to particular purposes in the body is not well-characterized and must be determined empirically.

The present invention still further contemplates the use of cilostazol. Cilostazol is a PDE III inhibitor that suppresses platelet aggregation and also acts as a direct arterial vasodilator. In addition ot its reported vasodilator and antiplatlet effects, cilostazol has been reported to have beneficial effect on plasma lipoproteins, increasing plasma high density lipoprotein cholesterol an apoliproprotein. See Dawson et al., *Circulation*, 98: 678–686 (1998); Elam et al., *Arterioscler Thromb. Vasc. Biol.*, 18: 1942–1947 (1998); *Drug Evaluation Monographs*, Vol. 99, Micromedex Inc.

The method of preparing cilostazol is described by Nish et al, *Chem. Pharm. Bull.*, 31: 1151 (1983) and in U.S. Pat. No. 4,277,479. Its pharmacology, metabolism, mechanism of action and clinical evaluations are described in *Arzneimittel-Forsch.* 35: 1117–1208 (1985).

While it is not necessary to understand any particular mechanism to carry out the present invention, it is believed that in some circumstances flosequinan and cilostazol can act as a direct-acting vasodilator to relax the corpus cavernosum smooth muscle cells, which in turn increases blood flow into the cavernosa space. This then leads to increased cavernosa pressure to produce an erect penis.

While the present invention is not limited to the treatment of a particular group, it is contemplated that the methods of the present invention comprise the utilization of pharmaceutical compounds and compositions to patients who are free of symptoms of cardiac disease and who have been treated with drugs which cause hypotensive effects such as nitrites and nitrates. In particular, citostazol may potentiate the hypotensive effects of nitrates, and its administration to patients who are concurrently using organic nitrates in any form may be contraindicated.

It is not intended that the present invention be limited by the particular nature of the therapeutic preparation. For example, the quinolines or quinolone derivatives can be provided together with physiologically tolerable liquid, gel or solid carriers, diluents, adjuvants and excipients. In addition, quinoline or quinolone analogs may be used together with other chemotherapeutic agents. On the other hand, formulations may also contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

While the present invention is not limited to a specific dosage level for flosequinan, for adult humans, the single dosage level per day is from 25 to 100 milligrams, preferably 50 to 75 milligrams.

Oral administration of flosequinan is effective, with a mean absolute bioavailability of 72%, following a single dose per day of 50 milligrams or 75 milligrams. Peak plasma concentrations of flosequinan are observed 1–2 hours following oral administration, while peak metabolite plasma levels are observed about seven hours following oral dosage.

Flosequinan is water soluble and is soluble in many organic solvents. Thus, while the present invention is not limited by the form of oral administration, aqueous and organic solutions of flosequinan for oral administration are contemplated. Likewise, flosequinan can be associated with a solid pharmaceutical carrier for solid oral administration, i.e., in pill form. One skilled in the art is able to readily prepare such solid formulations, which may include inactive ingredients such as croscarmellose sodium, hydroxypropyl methylcellulose, lactose, magnesium stearate, methocel ES, microcrystalline cellulose, povidine, propylene glycol and titanium dioxide.

However, it is not intended that flosequinan be limited to being administered orally. It can also be administered cutaneously, transurethrally, by standard injection or intracavernosally.

Flosequinan may also be administered cutaneously in a carrier adapted for tropical administration. Such carriers include creams, ointments, lotions, pastes, jellies, sprays, aerosols, bath oils, or other pharmaceutical carriers which accomplish direct contact between flosequinan and the pores of the skin. In general pharmaceutical preparations may comprise from about 0.001% to about 10% by w/w, and preferably from about 0.01 to 5% by w/w, of the active compound, flosequinan, in a suitable carrier. In some cases it may be necessary to dissolve the flosequinan in an appropriate solvent such as ethanol or DMSO (dimethylsulfoxide), and the like, to facilitate incorporation into a pharmaceutical preparation. Likewise, the present invention can be incorporated in other products associated with sexual activity. For example, a coated, erection inducing condom as disclosed in U.S. Pat. No. 4,829,991 and can be utilized with flosequinan or flosequinan in a pharmaceutical carrier as described above.

Injection can be carried out by any conventional injection means, employing an hypodermic syringe and needle or a similar device such as the NovolinPen sold by Squibb-Novo, Inc., Princeton, N.J., USA. This injection may be by the subject injecting himself or herself or by another person such as a partner during sexual relations or by a physician, prior to sexual relations. Methods for intracavernosal injection are described in U.S. Pat. No. 5,447,912 to Gerstenberg et al. One skilled in the art would be capable of injecting flosequinan with a carrier as described for intracavernosal injection.

Flosequinan can be introduced intracavernosally in a physiologically acceptable composition. Such compositions are aqueous solutions that are physiologically acceptable for administration by intracavernosal injection into the penis. The physiologically acceptable carrier is selected such that it is not painful or irritating upon intracavernosal injection. The physiologically acceptable compositions will preferably be sterile at the time of administration by intracavernosal injection.

Among the physiologically acceptable compositions for use in the methods is physiological saline or phosphate buffered saline, in which flosequinan is dissolved or suspended, such that the resulting composition is suitable for intracavernosal injection. A physiologically acceptable composition can also include a non-irritant preservative such as benzalkonium chloride at 0.05% w/v to 0./2% w/v. As the skilled artisan will understand, there are numerous non-toxic salts of VIP, PHM and $\alpha$-adrenergic blockers that can be employed in a physiologically acceptable composition for use in the methods herein, including, among others, the chloride, bromide, acetate, sulfate and mesylate salts.

As for cilostazol, it is administered in a therapeutic amount to a male or female suffering from symptoms of sexual dysfunction such that the symptoms are reduced. While the present invention is not limited to a specific dosage level, a single dosage per day of 25 to 150 milligrams, preferably 50 to 100 milligrams, for adult humans is contemplated. Multiple dosages are also contemplated.

Cilostazol may be administered orally to the patient. It can be administered as a tablet or capsule or as a pharmaceutical composition. Peak plasma concentrations of cilostazol are observed 2 to 4 hours following oral administration. See Suir et al., *J. Chin. Pharmacol.*, 38: 114–150 (1998); Niki et al., *Arzneimittel-Forsch.* 35: 173–1185 (1985). While the present invention is not limited by the form of oral administration, aqueous and organic solutions of cilostazol for oral administration are contemplated. The compositions may be formulated in a manner known to one skilled in the art, using pharmaceutically acceptable carriers suitable for use in such compositions that are also well known in the art. It is contemplated that the compositions of the present invention comprise 0.1–90% by weight of cilostazol. In a preferred embodiment, cilostazol can be prepared and administered in tablet form. The tablet is prepared by mixing cilostazol with an inert diluent such as lactose. See U.S. Pat. No. 5,627,191 to Birch et al.

In addition to being administered orally, cilostazol may also be administered cutaneously, intranasally, through respiratory inhalation or by standard injection.

While the present invention is not limited to the method of injecting cilostazol, it is preferred to inject cilostazol with a standard syringe. One skilled in the art would be capable of injecting cilostazol with a carrier as described for intracavenosal injection.

In carrying out the treatment, it is preferred that, for a period of between about 1 minutes and about 15 minutes, preferably about 5 to 10 minutes, the penis is constricted near the base thereof and between the base and the point at which the injection into a corpus cavernosum occurs, in order to limit loss of injected fluid from the corpus cavernosum before the ingredients in the fluid, that are active in inducing erection, have been able to have erection-inducing effects. The constriction can be effected by any means known in the art such as with a tourniquet, cuff, rubber band or the like, or even manually, in order to slow the release of the injected fluid and the pharmacologically active substance (s) therein into the general circulation.

Cilostazol may also be administered cutaneously in a carrier adapted for topical administration. Such carriers include creams, ointments, lotions, pastes, jellies, sprays, aerosols, bath oils, or other pharmaceutical carriers which accomplish directed contact between cilostazol and the pore of the skin. In some cases, it may be necessary to dissolve cilostazol in an appropriate organic solvent ot facilitate incorporation in to a pharmaceutical preparation. One skilled in the art is able to readily prepare such pharmaceutical formulations. See U.S. Pat. No. 5,719,197 to Kanios et al.

Cilostazol may also be administered intranasally. Formulations suitable for intranasal administration include ointments, creams, lotions, pastes, gels, sprays, aerosols, oils, and other pharmaceutical carriers which accomplish direct contact between cilostazol and the nasal cavity. Examples of pharmaceutical compositions administered intranasally are described in U.S. Pat. Nos. 5,393,773 and 5,554,639 to Crain et al., U.S. Pat. No. 5,603,943 to Yanagawa; and U.S. Pat. No. 5,801,161 to Merkus.

Cilostazol may also be administered through respiratory inhalation. Formulations suitable for respiratory inhalation include ointments, creams, lotions, pastes, gels, sprays, aerosols, oils, and other pharmaceutical carriers which accomplish direct contact between cilostazol and the respiratory tract. Examples of pharmaceutical compositions administered through respiratory inhalation are described in U.S. Pat. No. 4,552,891 to Hu et al., U.S. Pat. No. 5,869,479 to Kreutner et al., and U.S. Pat. No. 5,864,037 to Chasis et al.

In some embodiments, intranasal administration and respiratory inhalation of cilostazol are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacological agents to patients can be accomplished via aerosolization. Alternatively, the agent may be administered to the lung through a bronchoscope. Of course, the therapeutic agents may be investigated for their efficacy via other routes of administration, including parenteral administration.

The present invention is not limited by a particular method for introducing flosequinan or cilostazol transurethrally. In one embodiment, flosequinan or cilostazol is introduced to the urethra in a carrier as described for cutaneous administration. Devices and methods for transurethral introduction of pharmaceutical compositions is described in U.S. Pat. No. 5,474,535 to Place et al.,; Voss, U.S. Pat. No. 4,801,587 and Kock, EPA 0357581.

Additional methods of introducing flosequinan or cilostazol transurethrally include the use of medicated catheters, such as those used to prevent or treat localized infections and irritation of the urethra and bladder (see U.S. Pat. No. 4,640,912, hereby incorporated by reference). Alternatively, transurethral administration of pharmaceutical compositions is presented in U.S. Pat. Nos. 4,478,822, 4,610,868, 4,640,912 and 4,746,508 and medicated urethral suppositories, inserts or plugs, typically containing anti-infective agents or spermicide are disclosed in U.S. Pat. Nos. 1,897,423, 2,485,166, 2,696,209 and 3,373,746.

Likewise, the present PDE III inhibitors of the invention can be incorporated into other products associated with sexual activity. For example, a coated, erection inducing condom as disclosed in U.S. Pat. No. 4,829,991 can be utilized by coating the interior of the condom with the PDE III inhibitor such as cilostazol.

The administration of the compositions of the present invention is accomplished by sexual stimulation to induce an erection. The sexual stimulation can begin before or after the introduction of flosequinan or cilostazol. If the stimulation begins after the injection, it is preferably begun within 5 to 10 minutes to insure that there is significant overlap of the pharmacological effects of the pharmaceutical composition administered and the stimulative effects of the sexual stimulation. Whether the stimulation begins before or after the injection, it will continue preferably at least until an erection sufficient for vaginal penetration is achieved.

Sexual stimulation as prescribed by these methods, includes any form of sexual stimulation that would induce an erection in a normal male who is not suffering from erectile insufficiency. The sexual stimulation can be that which occurs in the course of sexual relations between the subject and another person or can be outside sexual relations with another person. Examples of methods of sexual stimulation include, alone or in combination, touching or erotically manipulating erogenous areas of the genital organs or other erogenous parts of the body; providing visual stimulation, as with a sexual explicit media or other form of sexually stimulative show or display. Additionally, providing vibratory stimulation to the penis, at between about 30 Hz and about 100 Hz with an amplitude of about 1 mm to about 5 ram, as can be provided, for example, by resting the penis on the table of a vibrating apparatus such as that of a Vibrector system.

In inducing an erection in an impotent male outside of sexual relations, as, for example, when a physician induces an erection in a patient suffering from psychogenic impotence, a preferred method of sexual stimulation includes providing visual stimulation, as with a pornographic film, simultaneously with vibratory stimulation of the penis, as with a Vibrector system set to between about 30 Hz and about 60 Hz (usually about 50 Hz)in frequency and between about 1 mm and about 2.5 mm (usually about 2.2 mm) in amplitude.

From the above, it should be clear that the present invention provides methods of treatment of male erectile dysfunction with pharmaceutical agents. In particular, quinolines and quinolones are administered therapeutically to patients having such dysfunction.

All publications and patents mentioned in this specification are herein incorporated by reference. Various modifications and variation of the described method and system of the invention will be apparent to those skilled in the art without departing from the scope and spirit of the invention. Although the invention has been described in connection with specifically preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of treating sexual dysfunction in humans by administering an effective amount of a PDE III selective inhibitor to relax corpus cavernosa smooth-muscle tissue in males or females, said inhibitor selected from the group consisting of 5-bromoquinoline, 5-nitroisoquinoline, 8-nitroisoquinoline, 3,4-dihydro-6-hydroxy-2(1H)-quinolone and 1 methylisoquinoline.

2. The method of claim 1, wherein the inhibitor is 5-bromoquinoline.

3. The method of claim 1, wherein the inhibitor is 5-nitroisoquinoline.

4. The method of claim 1, wherein the inhibitor is 8-nitroisoquinoline.

5. The method of claim 1, wherein the inhibitor is 1-methylisoquinoline.

6. The method of claim 1, wherein the effective amount is a single dosage per day of 25 to 150 milligrams.

7. The method of claim 1, wherein the inhibitor is 3,4-dihydro-6-hydroxy-2-(1H)-quinolone.

8. A method of treating sexual dysfunction in humans by administering an effective amount of compound selected from the group consisting of 5-bromoquinoline, 5-nitroisoquinoline, 8-nitroisoquinoline, 1-methylisoquinoline, and 3,4-dihydro-6-hydroxy-2(1H)-quinolone.

9. The method of claim 8, wherein the inhibitor is 5-bromoquinoline.

10. The method of claim 8, wherein the inhibitor is 5-nitroisoquinoline.

11. The method of claim 8, wherein the inhibitor is 8-nitroisoquinoline.

12. The method of claim 8, wherein the inhibitor is 1-methylisoquinoline.

13. The method of claim 8, wherein the inhibitor is 3,4-dihydro-6-hydroxy-2(1H)-quinolone.

* * * * *